US008652443B2

(12) United States Patent
Varanasi et al.

(10) Patent No.: US 8,652,443 B2
(45) Date of Patent: Feb. 18, 2014

(54) FOAMABLE MICROEMULSION COMPOSITIONS FOR TOPICAL ADMINISTRATION

(75) Inventors: Ravi K. Varanasi, North Providence, RI (US); Roman V. Rariy, Allston, MA (US)

(73) Assignee: Precision Dermatology, Inc., Cumberland, RI (US)

( * ) Notice: Subject to any disclaimer, the term of this patent is extended or adjusted under 35 U.S.C. 154(b) by 552 days.

(21) Appl. No.: 12/371,155

(22) Filed: Feb. 13, 2009

(65) Prior Publication Data

US 2009/0232743 A1 Sep. 17, 2009

Related U.S. Application Data

(60) Provisional application No. 61/028,586, filed on Feb. 14, 2008.

(51) Int. Cl.
*A61K 9/00* (2006.01)
*A61K 9/12* (2006.01)
*A61K 9/107* (2006.01)

(52) U.S. Cl.
USPC ............. 424/47; 514/945; 514/937; 514/817; 514/818

(58) Field of Classification Search
USPC ..................... 424/47; 514/945, 937, 817, 818
See application file for complete search history.

(56) References Cited

U.S. PATENT DOCUMENTS

| | | | |
|---|---|---|---|
| 2,801,201 A | 7/1957 | Kipnis | |
| 3,136,691 A | 6/1964 | Truant et al. | |
| 4,098,880 A | 7/1978 | Gaffar | |
| 4,174,295 A | 11/1979 | Bargigia et al. | |
| 4,291,087 A | 9/1981 | Warburton, Jr. | |
| 4,312,865 A | 1/1982 | Szucs | |
| 4,559,177 A | 12/1985 | Okutani et al. | |
| 4,600,575 A | 7/1986 | Lin et al. | |
| 4,699,843 A | 10/1987 | Charbonneau et al. | |
| 4,808,388 A | 2/1989 | Beutler et al. | |
| 4,870,174 A | 9/1989 | Paradies | |
| 5,116,603 A | 5/1992 | Friedman | |
| 5,118,494 A | 6/1992 | Schultz et al. | |
| 5,143,717 A | 9/1992 | Davis | |
| 5,290,539 A | 3/1994 | Marecki | |
| 5,433,191 A | 7/1995 | Haber et al. | |
| 5,446,070 A | 8/1995 | Mantelle | |
| 5,534,242 A | 7/1996 | Henry et al. | |
| 5,589,156 A | 12/1996 | Henry | |
| 5,593,661 A | 1/1997 | Henry | |
| 5,635,161 A | 6/1997 | Adjei et al. | |
| 5,679,325 A | 10/1997 | Henry | |
| 5,756,071 A | 5/1998 | Mattern et al. | |
| 5,858,331 A | 1/1999 | Henry et al. | |
| 5,980,867 A | 11/1999 | Tzou et al. | |
| 6,075,056 A | 6/2000 | Quigley, Jr. et al. | |
| 6,114,344 A | 9/2000 | Druzgala et al. | |
| 6,126,920 A | 10/2000 | Jones et al. | |
| 6,187,340 B1 | 2/2001 | Fukuta et al. | |
| 6,214,318 B1 | 4/2001 | Osipow et al. | |
| 6,235,265 B1 | 5/2001 | Logsdon | |
| 6,413,496 B1 | 7/2002 | Goodman et al. | |
| 6,432,415 B1 | 8/2002 | Osborne et al. | |
| 6,461,591 B1 | 10/2002 | Keller et al. | |
| 6,620,852 B2 | 9/2003 | Brogan et al. | |
| 6,743,413 B1 | 6/2004 | Schultz et al. | |
| 6,905,675 B2 | 6/2005 | Shacknai et al. | |
| 6,977,081 B1* | 12/2005 | Rood ........................... 424/401 |
| 2001/0031244 A1 | 10/2001 | Lewis et al. | |
| 2002/0022667 A1 | 2/2002 | Pace et al. | |
| 2002/0045670 A1 | 4/2002 | Lorant | |
| 2002/0058010 A1* | 5/2002 | Picard-Lesboueyries et al. ............................. 424/43 |
| 2002/0082317 A1 | 6/2002 | Lyons et al. | |
| 2003/0138381 A1 | 7/2003 | Duan et al. | |
| 2003/0144257 A1 | 7/2003 | Biggadike et al. | |
| 2004/0204492 A1 | 10/2004 | Shroot et al. | |
| 2005/0036950 A1 | 2/2005 | Jones et al. | |
| 2005/0042182 A1 | 2/2005 | Arkin et al. | |
| 2005/0255048 A1 | 11/2005 | Hirsh et al. | |
| 2005/0271598 A1* | 12/2005 | Friedman et al. ............... 424/47 |
| 2006/0140984 A1 | 6/2006 | Tamarkin et al. | |
| 2006/0188449 A1 | 8/2006 | Hirsh et al. | |
| 2006/0233721 A1 | 10/2006 | Tamarkin et al. | |
| 2007/0036731 A1 | 2/2007 | Hirsh et al. | |
| 2007/0154402 A1 | 7/2007 | Trumbore et al. | |
| 2008/0015271 A1 | 1/2008 | Abram et al. | |
| 2009/0048296 A1* | 2/2009 | Campbell et al. ............. 514/312 |

FOREIGN PATENT DOCUMENTS

| | | |
|---|---|---|
| EP | 0 372 777 | 6/1990 |
| EP | 1 468 678 | 10/2004 |
| WO | WO-85/01876 | 5/1985 |
| WO | WO-91/04011 | 4/1991 |

(Continued)

OTHER PUBLICATIONS

International Search Report dated Oct. 6, 2010 from PCT/US2010/022375.

Allen, et al.; "Iatrogenic methemoglobinemia from benzocaine spray in trauma"; American Journal of Emergency Medicine 22(3): 226 (2004).

Byrne, "The need for caution with topical anesthesia during endoscopic procedures, as liberal use may result in methemoglobinemia"; J. Clinc. Gastroenterol. 38(3): 225-229 (2004).

(Continued)

*Primary Examiner* — Mina Haghighatian
(74) *Attorney, Agent, or Firm* — Foley Hoag LLP

(57) ABSTRACT

Described are ethanol-free foamable microemulsions for topical application, and method of making them. The propellants used in the compositions may be environmentally-friendly hydrofluoroalkanes. The foam compositions may also comprise one or more of a variety of active ingredients, including anti-inflammatory agents, anesthetics, and keratolytic agents.

2 Claims, 8 Drawing Sheets

(56) References Cited

FOREIGN PATENT DOCUMENTS

| WO | WO-92/06675 | 4/1992 |
|---|---|---|
| WO | WO-92/08447 | 5/1992 |
| WO | WO-93/24107 | 12/1993 |
| WO | WO-96/03115 | 2/1996 |
| WO | WO-99/02211 | 1/1999 |
| WO | WO-2004037225 | 5/2004 |
| WO | WO-2005016329 | 2/2005 |
| WO | WO-2005/032522 | 4/2005 |
| WO | WO-2007/050543 | 5/2007 |

OTHER PUBLICATIONS

Dalziel and Creazzo, "Pharmaceutical Aerosols", Spray Technology and Marketing 6:19-24 (2003).

Douglas, "Methemoglobinemia induced by a topical anesthetic spray (cetacaine)" Chest 71(5): 587-591 (1977).

Garcia, "Etidocaine—A long-acting anesthestic agent" Anesthesia Progress 29(1): 12-13 (1982).

Guertler, et al., "Topical Anesthetic-Induced Methemoglobinemia in sheep: A comparison of benzocaine and lidocaine" Fundemental and Applied Toxicology, 18: 294-298 (1992).

Ho, Hsiu-O; et al. "Preparation of Microemulsions using polyglycerol fatty acid esters as surfactant for delivery of protein drugs." *Journal of Pharmaceutical Sciences*, vol. 85(2), Feb. 1996, 138-143.

Karim, et al., "Methemoglobinemia complicating topical lidocaine used during endoscopic procedures" American Journal of Medicine 111(2): 150-153 (2001).

Khorasani, "Canister tip orientation and residual volume have significant impact on the dose of benzocaine delivered by Hurricaine spray" Anesthesia and Analgesia 92(2): 379-383 (2001).

Kuschner, "Benzocaine-associated methemoglobinemia following bronchoscopy in a healthy research participant" Respir. Care 45(8): 953-956 (2000).

Lee, Philip J.; et al. "Novel microemulsion enhancer formulation for simultaneous transdermal delivery of hydrophilic and hydrophobic drugs." *Pharmaceutical Research,* vol. 20, Feb. 2003, 264-269.

Mei, Zhinan; et al. "Solid lipid nanoparticle and microemulsion for topical delivery of triptolide." European Journal of Pharmaceutics and Biopharmaceutics 56 (2003) 189-196.

Meintertz, Jeffery, R., et al.; "Liquid chromatographic determination of benzocaine and N-acetylbenzocaine in the edible fillet tissue from rainbow trout," Journal of Chromatography A, 855 (1999) 255-260.

*Metered Dose Inhaler Technology* (Purewal, et al. eds.), pp. 54-59, CRC Press LLC: Boca Raton, Florida, (1998).

Novaro, et al., "Benzocaine-induced methemoglobinemia: Experience from a high-volume transesophageal echocardiography laboratory" Journal of the American Society of Echocardiography 16(2): 170-175 (2003).

Purdon, et al., "Foam Drug Delivery in Dermatology: Beyond the Scalp Foam Drug Delivery in Dermatology: Beyond the Scalp", American Journal of Drug Delivery, 1(1):71-75 (2003).

Roth, et al.; "Airway Inflammation in Young Marijuana and Tobacco Smokers," Am. J. Respir Crit Care Med; vol. 157. pp. 928-937, 1998.

Topical agents. http://coventry.formularies.com/single_drug_disp.asp?drugname=Butamben-Tetracaine-Benzocaine&drugtype=2. Copyright 2002. Accessed Mar. 3, 2009.

Waste and Air Pollutants Found in Hospitals, Virtual Library of Sustainable Development and Environmental Health, [online], [retrieved on Dec. 2, 2008]. Retrieved from Virtual Library of Sustainable Development and Environmental Health, Panamerica Health Organization, Regional Office of the World Health Organization, Area of Sustainable Development and Environmental Health using the Internet (URL: http://www.bvsde.paho.org/bvsacd/cd48/practices/anex.4.pdf).

ISR from PCT/US2006/041366 (date mailed Jun. 25, 2007).

ISR from PCT/US2004/032714 (dated mailed Feb. 23, 2005).

\* cited by examiner

FOAMABLE MICROEMULSION COMPOSITIONS FOR TOPICAL ADMINISTRATION

RELATED APPLICATIONS

This application claims the benefit of priority to U.S. Provisional Patent Application Ser. No. 61/028,586, filed Feb. 14, 2008; the contents of which are hereby incorporated by reference in its entirety.

FIELD OF THE INVENTION

The present invention is in the field of foamable microemulsion compositions for topical administration.

BACKGROUND OF THE INVENTION

Microemulsions are thermodynamically-stable, optically-clear emulsions having submicron-sized droplets suspended in a continuous phase. These emulsions form spontaneously and typically consist of an aqueous phase, an organic phase, and a surfactant/co-surfactant component.

Previous data suggest that ethanol is required to maintain stable oil-in-water microemulsions. However, topical application of ethanol has a drying effect on the skin. Additionally, ethanol and compositions containing ethanol are extremely flammable. For these reasons, ethanol-containing microemulsions for topical application have seen limited commercial use.

SUMMARY OF THE INVENTION

In certain embodiments, the present invention relates to a composition comprising: an aqueous phase, from about 15% to about 40% by weight; a co-surfactant, from about 10% to about 20% by weight; an active agent, from about 0.01% to about 10% by weight; a surfactant, from about 15% to about 40% by weight; a propellant, from about 5% to about 15% by weight, wherein the propellant is a hydrofluoroalkane; and an oil phase, from about 10% to about 35% by weight. In certain embodiments, the present invention relates to a composition comprising: water, from about 15% to about 30% by weight; a co-surfactant, from about 10% to about 20% by weight; an active agent, from about 0.01% to about 10% by weight; a surfactant, from about 30% to about 40% by weight; a propellant, from about 5% to about 15% by weight, wherein the propellant is a hydrofluoroalkane; and isopropyl myristate, from about 10% to about 20% by weight. In certain embodiments, the present invention relates to any one of the above-mentioned compositions, wherein the composition does not comprise ethanol. In certain embodiments, the compositions of the present invention produce foam upon actuation by an aerosol container.

In certain embodiments, the invention relates to a method of preparation, comprising first formulating an active agent-containing microemulsion concentrate, then placing the concentrate into an aerosol container and, lastly, mixing the concentrate and pressurizing the container with a propellant to result in a stable, optically-clear propellant-containing microemulsion.

DETAILED DESCRIPTION OF THE INVENTION

Figure 1:
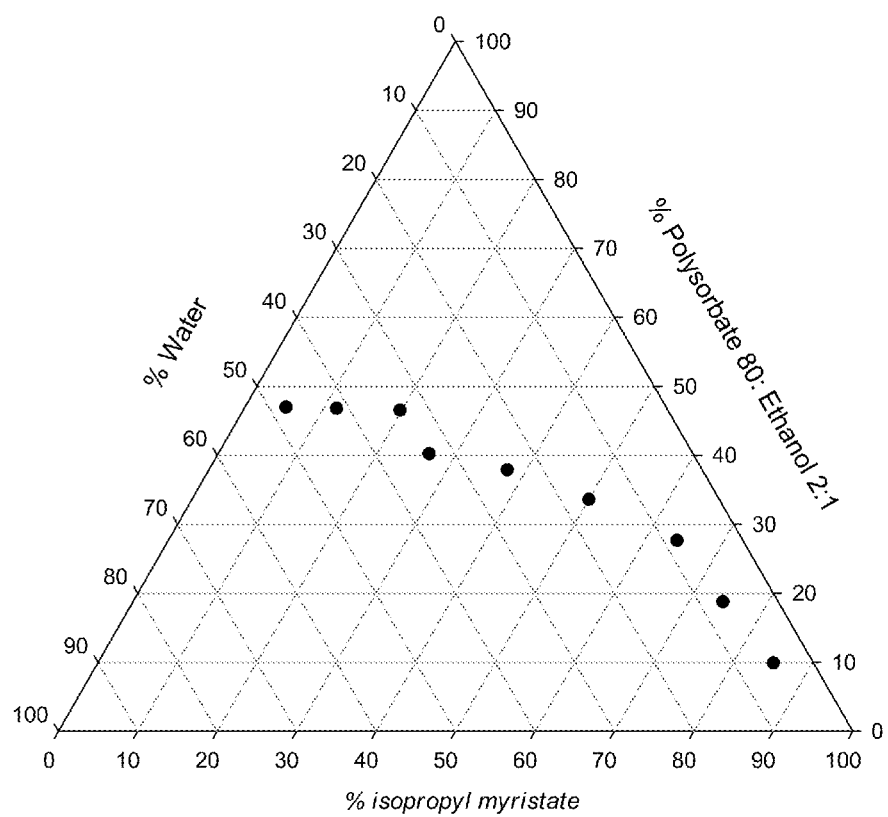
FIG. 1 depicts a ternary phase diagram for microemulsion systems comprising water (left axis), isopropyl myristate (bottom axis), and polysorbate 80:ethanol (2:1) (right axis).

One aspect of the invention relates to a composition comprising a stable, optically-clear microemulsion. In certain embodiments, the invention relates to an above-mentioned composition, wherein the microemulsion comprises water, co-surfactant, surfactant, emulsifier, and preservative. In certain embodiments, the invention relates to any one of the above-mentioned compositions, wherein the microemulsion further comprises an active agent. In certain embodiments, the invention relates to any one of the above-mentioned compositions, wherein the microemulsion does not comprise ethanol.

In one embodiment, one or more other solvents can substitute for ethanol in the formulation of microemulsions. In one embodiment, propylene glycol is used in the microemulsion instead of ethanol. When mixed in certain ratios, ternary systems of water, isopropyl myristate, and polysorbate 80:propylene glycol (2.5:1) allow a clear microemulsion to be formed (see, e.g., FIG. 2). Surprisingly, these systems exhibit phase behavior similar to systems containing ethanol (compare FIG. 2 to FIG. 1). Microemulsions formulated using the ternary system of water, isopropyl myristate, and polysorbate 80:propylene glycol (2.5:1) resulted in optically-clear, thermodynamically-stable microemulsions. These microemulsions maintained the active ingredient in solution without disrupting microemulsion structure.

In certain embodiments, the active agent-containing microemulsion, upon mixing with a propellant in a pressurized container, remains a single-phase, optically-clear microemulsion. Upon actuation from an aerosol container, microemulsions of the present invention produce foam.

Exemplary identities of various constituents of the compositions of the present invention are described below.

1. Propellants

In certain embodiments, the propellant is a HFA or a mixture of one or more hydrofluorocarbons. Suitable hydrofluorocarbons include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. The concentration of the HFA propellant is from about 2% to about 30% by weight of the concentrate. Hydrocarbon as well as CFC propellants can also be used in the present invention.

2. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

2.1 Antibiotics

Representative antibiotics include, without limitation, benzoyl peroxide, octopirox, erythromycin, zinc, tetracyclin, triclosan, azelaic acid and its derivatives, phenoxy ethanol and phenoxy propanol, ethyl acetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin. Mixtures of these antibiotic agents may also be employed. Additionally, dermatologically-acceptable salts and esters of any of these agents may be employed.

2.2 Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac, fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamiate, a flufenamic acid derivative, is particularly useful for topical application.

2.3 Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

2.4 Anesthetics

Suitable anesthetics include the aminoacylanilide compounds such as lidocaine, prilocalne, bupivacaine, levo-bupivacaine, ropivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, butamben, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amide compounds such as dibucaine and related local anesthetic compounds; aminoketone compounds such as falicaine, dyclonine and related local anesthetic compounds; and amino ether compounds such as pramoxine, dimethisoquien, and related local anesthetic compounds; and para-amino benzoic acid esters such as benzocaine. Other suitable local anesthetics include ketocaine, dibucaine, amethocaine, propanacaine, and propipocaine.

2.5 Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, framesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

2.6 Keratolytic Agents

Suitable keratolytic agents include, but are not limited to, urea, salicylic acid, papain, sulfur, glycolic acid, pyruvic acid, resorcinol, N-acetylcysteine, retinoids such as retinoic acid and its derivatives (e.g., cis and trans, esters), alpha hydroxy acids, beta hydroxy acids, coal tar, and combinations thereof.

2.7 Other Agents

Suitable other agents include, but are not limited to, deodorant agents, antiperspirants, sun screening agents, sunless tanning agents, vitamins, hair conditioning agents, anti-irritants, and combinations thereof.

Examples of skin-soothing agents include, but are not limited to, aloe, avocado oil, green tea extract, hops extract, chamomile extract, colloidal oatmeal, calamine, cucumber extract, and combinations thereof.

Examples of vitamins include, but are not limited to, vitamins A, D, E, K, and combinations thereof.

Examples of sunscreens include, but are not limited to, p-Aminobenzoic acid, Avobenzone, Cinoxate, Dioxybenzone, Homosalate, Menthyl anthranilate, Octocrylene, Octyl methoxycinnamate, Octyl salicylate, Oxybenzone, Padimate 0, Phenylbenzimidazole sulfonic acid, Sulisobenzone, Titanium dioxide, Trolaminie salicylate, Zinc oxide, 4-methyl-benzylidene camphor, Methylene Bis-Benzotriazolyl Tetramethylbutylphenol, Bis-Ethylhexyloxyphenol Methoxyphenyl Triazine, Terephthalylidene Dicamphor Sulfonic Acid, Drometrizole Trisiloxane, Disodium Phenyl Dibenzimidazole Tetrasulfonate, Diethylamino Hydroxybenzoyl Hexyl Benzoate, Octyl Triazone, Diethylhexyl Butamido Triazone, Polysilicone-15, and combinations thereof.

3. Additional Active Agents

The compositions optionally contain one or more additional pharmaceutically active agent. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

4. Surfactants and Emulsifiers

Surfactants suitable for use in the present invention may be ionic or non-ionic. These include, but are not limited to: polysorbates, sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyethylene alkyl ethers, dioctyl sodium sulphosuccinate, caprylocaproyl macrogol-8 glycerides (Labrasol®), polyoxyl castor oil, nonylphenol ethoxylate, cyclodextrins, lecithin, and methylbenzethonium chloride.

Many of these surfactants may also serve as emulsifiers in formulations of the present invention.

5. Co-surfactants

A co-surfactant is a surface-active agent that acts in addition to the surfactant by further lowering the interfacial energy, but that would not effectively function alone as a surfactant. For example, short-chain alcohols are found to concentrate in the surfactant layer of aggregates, replacing surfactant molecules and leading to a decrease in the aggregation number, and an increase in the number of aggregates. These molecules directly influence the properties of the aggregates.

Suitable co-surfactants of the present invention include, but are not limited to, ethanol, propylene glycol, 1-butanol, 1-decanol, and combinations of any of them. Furthermore, medium chain alcohols, oleic esters of polyglycerol, polyglyceryl-3-oleate (Plurol Oleique®), polyglyceryl isostearate, or polyglyceryl-6 isostearate (Plurol Isostearique®) may also be employed separately or in combination with any other co-surfactant.

6. Aqueous Phase

In certain embodiments, a composition of the present invention is an oil-in-water emulsion. Suitable components for use in formulating the aqueous phase of such an oil-in-water emulsion include water, aqueous buffers with various pH levels (e.g., pH about 2, pH about 3, pH about 4, pH about 5, pH about 6, pH about 7, pH about 8, pH about 9, pH about 10, pH about 11, or pH about 12), and water-miscible solvents, such as glycols, glycerol, liquid polyols, and dimethyl sulfoxide. One or more aqueous component may be present.

7. Oil Phase

In certain embodiments, a composition of the present invention is an oil-in-water emulsion. Suitable components for use in formulating the oil phase of such an oil-in-water microemulsion include, but are not limited to, mineral oil, emollient oils, saturated fatty acids, unsaturated fatty acids, medium chain-length triglycerides, isopropyl myristate, isopropyl palmitate, oleic acid, isostearylic isostearate, triacetin, ethyl oleate, and octyl octanoate.

8. Preservatives and Antioxidants

Suitable preservatives for use in the present invention include, but are not limited to: ureas, such as imidazolidinyl urea and diazolidinyl urea; phenoxyethanol; sodium methyl paraben, methylparaben, ethylparaben, and propylparaben; potassium sorbate; sodium benzoate; citric acid; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; and alcoholic agents, for example, chlorobutanol, phenylethyl alcohol, and benzyl alcohol.

Suitable antioxidants include, but are not limited to, ascorbic acid and its esters, sodium bisulfite, butylated hydroxytoluene, butylated hydroxyanisole, tocopherols, and chelating agents like EDTA and citric acid.

9. Additional Constituents

Additional constituents suitable for incorporation into the microemulsions of the present invention include, but are not limited to: protectives, adsorbents, demulcents, emollients, moisturizers, buffering agents, solubilizing agents, and skin-penetration agents.

Often, one constituent of a composition may accomplish several functions. In certain embodiments, the present invention relates to constituents that may act as a lubricant, an emollient, or a skin-penetrating agent. In certain embodiments, the multi-functional constituent is isostearylic isostearate, isopropyl isostearate, isopropyl palmitate, or isopropyl myristate.

Exemplary Compositions

In certain embodiments, the present invention relates to a composition, comprising an aqueous phase, from about 15% to about 40% by weight;

a co-surfactant, from about 10% to about 20% by weight;

an active agent, from about 0.01% to about 10% by weight;

a surfactant, from about 15% to about 40% by weight;

a propellant, from about 5% to about 15% by weight, wherein the propellant is a hydrofluoroalkane; and an oil phase, from about 10% to about 35% by weight.

In certain embodiments, the present invention relates to a composition consisting essentially of an aqueous phase, from about 15% to about 40% by weight;

a co-surfactant, from about 10% to about 20% by weight;

an active agent, from about 0.01% to about 10% by weight;

a surfactant, from about 15% to about 40% by weight;

a propellant, from about 5% to about 15% by weight, wherein the propellant is a hydrofluoroalkane; and an oil phase, from about 10% to about 35% by weight.

In certain embodiments, the present invention relates to a composition consisting of an aqueous phase, from about 15% to about 40% by weight;

a co-surfactant, from about 10% to about 20% by weight;

an active agent, from about 0.01% to about 10% by weight;
a surfactant, from about 15% to about 40% by weight;
a propellant, from about 5% to about 15% by weight, wherein the propellant is a hydrofluoroalkane; and
an oil phase, from about 10% to about 35% by weight.

In certain embodiments, the present invention relates to any one of the above-mentioned compositions, wherein the oil phase is selected from the group consisting of mineral oil, emollient oils, saturated fatty acids, unsaturated fatty acids, medium chain-length triglycerides, isopropyl myristate, isopropyl palmitate, oleic acid, isostearylic isostearate, triacetin, ethyl oleate, and octyl octanoate.

In certain embodiments, the present invention relates to any one of the above-mentioned compositions, wherein the oil phase is isopropyl myristate.

In certain embodiments, the present invention relates to any one of the above-mentioned compositions, wherein the oil phase is present in a quantity from about 10% to about 20% by weight.

In certain embodiments, the present invention relates to a composition, comprising
water, from about 15% to about 30% by weight;
a co-surfactant, from about 10% to about 20% by weight;
an active agent, from about 0.01% to about 10% by weight;
a surfactant, from about 30% to about 40% by weight;
a propellant, from about 5% to about 15% by weight, wherein the propellant is a hydrofluoroalkane; and
isopropyl myristate, from about 10% to about 20% by weight.

In certain embodiments, the present invention relates to a composition consisting essentially of
water, from about 15% to about 30% by weight;
a co-surfactant, from about 10% to about 20% by weight;
an active agent, from about 0.01% to about 10% by weight;
a surfactant, from about 30% to about 40% by weight;
a propellant, from about 5% to about 15% by weight, wherein the propellant is a hydrofluoroalkane; and
isopropyl myristate, from about 10% to about 20% by weight.

In certain embodiments, the present invention relates to a composition consisting of water, from about 15% to about 30% by weight;
a co-surfactant, from about 10% to about 20% by weight;
an active agent, from about 0.01% to about 10% by weight;
a surfactant, from about 30% to about 40% by weight;
a propellant, from about 5% to about 15% by weight, wherein the propellant is a hydrofluoroalkane; and
isopropyl myristate, from about 10% to about 20% by weight.

In certain embodiments, the present invention relates to any one of the above-mentioned compositions, wherein the composition does not comprise ethanol.

In certain embodiments, the present invention relates to any one of the above-mentioned compositions, wherein water is present in a quantity from about 17% to about 25% by weight. In certain embodiments, the present invention relates to any one of the above-mentioned compositions, wherein water is present in a quantity from about 18% to about 24% by weight. In certain embodiments, the present invention relates to any one of the above-mentioned compositions, wherein water is present in about 18%, about 19%, about 20%, about 21%, about 22%, about 23%, or about 24% by weight. In certain embodiments, the present invention relates to any one of the above-mentioned compositions, wherein water is present in about 18% by weight. In certain embodiments, the present invention relates to any one of the above-mentioned compositions, wherein water is present in about 20% by weight. In certain embodiments, the present invention relates to any one of the above-mentioned compositions, wherein water is present in about 24% by weight.

In certain embodiments, the present invention relates to any one of the above-mentioned compositions, wherein the co-surfactant is ethylene glycol, propylene glycol, or glycerol.

In certain embodiments, the present invention relates to any one of the above-mentioned compositions, wherein the co-surfactant is propylene glycol.

In certain embodiments, the present invention relates to any one of the above-mentioned compositions, wherein the co-surfactant is present in a quantity from about 11% to about 18% by weight. In certain embodiments, the present invention relates to any one of the above-mentioned compositions, wherein the co-surfactant is present in a quantity from about 12% to about 17% by weight. In certain embodiments, the present invention relates to any one of the above-mentioned compositions, wherein the co-surfactant is present in about 13%, about 14%, about 15%, or about 16% by weight. In certain embodiments, the present invention relates to any one of the above-mentioned compositions, wherein the co-surfactant is present in about 13% by weight. In certain embodiments, the present invention relates to any one of the above-mentioned compositions, wherein the co-surfactant is present in about 14% by weight. In certain embodiments, the present invention relates to any one of the above-mentioned compositions, wherein the co-surfactant is present in about 15% by weight. In certain embodiments, the present invention relates to any one of the above-mentioned compositions, wherein the co-surfactant is present in about 16% by weight.

In certain embodiments, the present invention relates to any one of the above-mentioned compositions, wherein the active agent is selected from the group consisting of an antibiotic agent, an anti-inflammatory agent, an anesthetic, an antimicrobial agent, and a keratolytic agent.

In certain embodiments, the present invention relates to any one of the above-mentioned compositions, wherein the active agent is present in a quantity from about 0.05% to about 8.0% by weight. In certain embodiments, the present invention relates to any one of the above-mentioned compositions, wherein the active agent is present in a quantity from about 0.06% to about 7% by weight. In certain embodiments, the present invention relates to any one of the above-mentioned compositions, wherein the active agent is present in about 0.06%, about 0.07%, about 0.08%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5.0%, about 5.5%, about 6.0%, about 6.5%, or about 7.0% by weight.

In certain embodiments, the present invention relates to any one of the above-mentioned compositions, wherein the active agent is an anesthetic.

In certain embodiments, the present invention relates to any one of the above-mentioned compositions, wherein the anesthetic is lidocaine.

In certain embodiments, the present invention relates to any one of the above-mentioned compositions, wherein the anesthetic is present in a quantity from about 1% to about 6% by weight. In certain embodiments, the present invention relates to any one of the above-mentioned compositions, wherein the anesthetic is present in a quantity from about 2% to about 5% by weight. In certain embodiments, the present invention relates to any one of the above-mentioned compositions, wherein the anesthetic is present in about 2.0%, about 2.5%, about 3.0%, about 3.5%, about 4.0%, about 4.5%, or about 5.0% by weight. In certain embodiments, the present invention relates to any one of the above-mentioned compositions, wherein the anesthetic is present in about 3.5% by weight. In certain embodiments, the present invention relates to any one of the above-mentioned compositions, wherein the anesthetic is present in about 4.0% by weight. In certain embodiments, the present invention relates to any one of the above-mentioned compositions, wherein the anesthetic is present in about 4.5% by weight.

In certain embodiments, the present invention relates to any one of the above-mentioned compositions, wherein the active agent is an anti-inflammatory agent.

In certain embodiments, the present invention relates to any one of the above-mentioned compositions, wherein the anti-inflammatory agent is a non-steroidal anti-inflammatory agent or a steroidal anti-inflammatory agent.

In certain embodiments, the present invention relates to any one of the above-mentioned compositions, wherein the steroidal anti-inflammatory agent is triamcinolone acetonide or betamethasone dipropionate.

In certain embodiments, the present invention relates to any one of the above-mentioned compositions, wherein the steroidal anti-inflammatory agent is triamcinolone acetonide.

In certain embodiments, the present invention relates to any one of the above-mentioned compositions, wherein the steroidal anti-inflammatory agent is betamethasone dipropionate.

In certain embodiments, the present invention relates to any one of the above-mentioned compositions, wherein the anti-inflammatory agent is present in a quantity from about 0.05% to about 1.5% by weight. In certain embodiments, the present invention relates to any one of the above-mentioned compositions, wherein the anti-inflammatory agent is present in a quantity from about 0.06% to about 1.0% by weight. In certain embodiments, the present invention relates to any one of the above-mentioned compositions, wherein the anti-inflammatory agent is present in about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1.0% by weight. In certain embodiments, the present invention relates to any one of the above-mentioned compositions, wherein the anti-inflammatory agent is present in about 0.08% by weight. In certain embodiments, the present invention relates to any one of the above-mentioned compositions, wherein the anti-inflammatory agent is present in about 0.09% by weight. In certain embodiments, the present invention relates to any one of the above-mentioned compositions, wherein the anti-inflammatory agent is present in about 0.1% by weight.

In certain embodiments, the present invention relates to any one of the above-mentioned compositions, wherein the active agent is a keratolytic agent.

In certain embodiments, the present invention relates to any one of the above-mentioned compositions, wherein the keratolytic agent is salicylic acid.

In certain embodiments, the present invention relates to any one of the above-mentioned compositions, wherein the keratolytic agent is present in a quantity from about 2.0% to about 8.0% by weight. In certain embodiments, the present invention relates to any one of the above-mentioned compositions, wherein the keratolytic agent is present in a quantity from about 3.0% to about 7.0% by weight. In certain embodiments, the present invention relates to any one of the above-mentioned compositions, wherein the keratolytic agent is present in about 3.0%, about 3.5%, about 4.0%, about 4.5%, about 5.0%, about 5.5%, about 6.0%, about 6.5%, or about 7.0% by weight. In certain embodiments, the present invention relates to any one of the above-mentioned compositions, wherein the keratolytic agent is present in about 5.0% by weight. In certain embodiments, the present invention relates to any one of the above-mentioned compositions, wherein the keratolytic agent is present in about 5.5% by weight. In certain embodiments, the present invention relates to any one of the above-mentioned compositions, wherein the keratolytic agent is present in about 6.0% by weight.

In certain embodiments, the present invention relates to any one of the above-mentioned compositions, wherein the active agent is a skin-soothing agent.

In certain embodiments, the present invention relates to any one of the above-mentioned compositions, wherein the skin-soothing agent is aloe vera.

In certain embodiments, the present invention relates to any one of the above-mentioned compositions, wherein the skin-soothing agent is present in a quantity from about 0.05% to about 2.0% by weight. In certain embodiments, the present invention relates to any one of the above-mentioned compositions, wherein the skin-soothing agent is present in a quantity from about 0.08% to about 1.5% by weight. In certain embodiments, the present invention relates to any one of the above-mentioned compositions, wherein the skin-soothing agent is present in about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, or about 1.5% by weight. In certain embodiments, the present invention relates to any one of the above-mentioned compositions, wherein the skin-soothing agent is present in about 0.08% by weight. In certain embodiments, the present invention relates to any one of the above-mentioned compositions, wherein the skin-soothing agent is present in about 0.09% by weight.

In certain embodiments, the present invention relates to any one of the above-mentioned compositions, wherein the skin-soothing agent is present in about 0.1% by weight.

In certain embodiments, the present invention relates to any one of the above-mentioned compositions, further comprising a second active agent.

In certain embodiments, the present invention relates to any one of the above-mentioned compositions, wherein the surfactant is selected from the group consisting of polysorbates, sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, and methylbenzethonium chloride In certain embodiments, the present invention relates to any one of the above-mentioned compositions, wherein the surfactant is a polysorbate.

In certain embodiments, the present invention relates to any one of the above-mentioned compositions, wherein the surfactant is polysorbate 80.

In certain embodiments, the present invention relates to any one of the above-mentioned compositions, wherein the surfactant is present in a quantity from about 32% to about 39% by weight. In certain embodiments, the present invention relates to any one of the above-mentioned compositions, wherein the surfactant is present in a quantity from about 33% to about 39% by weight. In certain embodiments, the present invention relates to any one of the above-mentioned compositions, wherein the surfactant is present in about 33%, about 34%, about 35%, about 36%, about 37%, about 38%, or about 39% by weight. In certain embodiments, the present invention relates to any one of the above-mentioned compositions, wherein the surfactant is present in about 34% by weight. In certain embodiments, the present invention relates to any one of the above-mentioned compositions, wherein the surfactant is present in about 36% by weight. In certain embodiments, the present invention relates to any one of the above-mentioned compositions, wherein the surfactant is present in about 38% by weight.

In certain embodiments, the present invention relates to any one of the above-mentioned compositions, wherein the hydrofluoroalkane is 1,1,1,2,3,3,3-heptafluoropropane, 1,1,1,2-tetrafluoroethane, or a mixture thereof.

In certain embodiments, the present invention relates to any one of the above-mentioned compositions, wherein the hydrofluoroalkane is 1,1,1,2-tetrafluoroethane.

In certain embodiments, the present invention relates to any one of the above-mentioned compositions, wherein the propellant is present in a quantity from about 5% to about 13% by weight. In certain embodiments, the present invention relates to any one of the above-mentioned compositions, wherein the propellant is present in a quantity from about 6% to about 13% by weight. In certain embodiments, the present invention relates to any one of the above-mentioned compositions, wherein the propellant is present in about 6%, about 7%, about 8%, about 9%, about 10%, about 11%, about 12%, or about 13% by weight. In certain embodiments, the present invention relates to any one of the above-mentioned compositions, wherein the propellant is present in about 6% by weight. In certain embodiments, the present invention relates to any one of the above-mentioned compositions, wherein the propellant is present in about 12% by weight.

In certain embodiments, the present invention relates to any one of the above-mentioned compositions, further comprising a preservative.

In certain embodiments, the present invention relates to any one of the above-mentioned compositions, wherein the preservative is selected from the group consisting of ureas; phenoxyethanol; sodium methyl paraben, methylparaben, ethylparaben, and propylparaben; potassium sorbate; sodium benzoate; citric acid; chlorine dioxide; quaternary ammonium compounds; mercurial agents; and alcoholic agents.

In certain embodiments, the present invention relates to any one of the above-mentioned compositions, wherein the preservative is a quaternary ammonium compound, an alcoholic agent, or a combination of both.

In certain embodiments, the present invention relates to any one of the above-mentioned compositions, wherein the preservative is benzalkonium chloride.

In certain embodiments, the present invention relates to any one of the above-mentioned compositions, wherein the preservative is benzyl alcohol.

In certain embodiments, the present invention relates to any one of the above-mentioned compositions, wherein the preservative is a combination of benzalkonium chloride and benzyl alcohol.

In certain embodiments, the present invention relates to any one of the above-mentioned compositions, wherein the preservative is present in a quantity from about 0.005% to about 3% by weight. In certain embodiments, the present invention relates to any one of the above-mentioned compositions, wherein the preservative is present in a quantity from about 0.01% to about 2.5% by weight. In certain embodiments, the present invention relates to any one of the above-mentioned compositions, wherein the preservative is present in about 0.01%, about 0.02%, about 0.03%, about 0.04%, about 0.05%, about 0.06%, about 0.07%, about 0.08%, about 1.0%, about 1.5%, about 2.0%, or about 2.5% by weight.

In certain embodiments, the present invention relates to any one of the above-mentioned compositions, wherein the benzalkonium chloride is present in a quantity from about 0.005% to about 0.1% by weight. In certain embodiments, the present invention relates to any one of the above-mentioned compositions, wherein the benzalkonium chloride is present in a quantity from about 0.008% to about 0.08% by weight. In certain embodiments, the present invention relates to any one of the above-mentioned compositions, wherein the benzalkonium chloride is present in about 0.008%, about 0.009%, about 0.01%, about 0.02%, about 0.03%, about 0.04%, about 0.05%, about 0.06%, about 0.07%, or about 0.08% by weight. In certain embodiments, the present invention relates to any one of the above-mentioned compositions, wherein the benzalkonium chloride is present in about 0.01% by weight. In certain embodiments, the present invention relates to any one of the above-mentioned compositions, wherein the benzalkonium chloride is present in about 0.02% by weight. In certain embodiments, the present invention relates to any one of the above-mentioned compositions, wherein the benzalkonium chloride is present in about 0.04% by weight.

In certain embodiments, the present invention relates to any one of the above-mentioned compositions, wherein the benzyl alcohol is present in a quantity from about 0.8% to about 3.0% by weight. In certain embodiments, the present invention relates to any one of the above-mentioned compositions, wherein the benzyl alcohol is present in a quantity from about 1.2% to about 2.5% by weight. In certain embodiments, the present invention relates to any one of the above-mentioned compositions, wherein the benzyl alcohol is present in about 1.2%, about 1.3%, about 1.4%, about 1.5%, about 1.6%, about 1.7%, about 1.8%, about 1.9%, about 2.0%, about 2.1%, about 2.2%, about 2.3%, about 2.4% or about 2.5% by weight. In certain embodiments, the present invention relates to any one of the above-mentioned compositions, wherein the benzyl alcohol is present in about 1.4% by weight. In certain embodiments, the present invention relates to any one of the above-mentioned compositions, wherein the benzyl alcohol is present in about 1.5% by weight. In certain embodiments, the present invention relates to any one of the above-mentioned compositions, wherein the benzyl alcohol is present in about 2.1% by weight.

A composition comprising
water, from about 15% to about 40% by weight;
a co-surfactant, from about 10% to about 20% by weight;
an active agent, from about 0.01% to about 10% by weight;
a surfactant, from about 15% to about 40% by weight;
a propellant, from about 5% to about 15% by weight, wherein the propellant is a hydrofluoroalkane;
a preservative, from about 0.005% to about 3.0% by weight; and
isopropyl myristate, from about 10% to about 35% by weight.

A composition consisting essentially of water, from about 15% to about 40% by weight;
a co-surfactant, from about 10% to about 20% by weight;
an active agent, from about 0.01% to about 10% by weight;
a surfactant, from about 15% to about 40% by weight;
a propellant, from about 5% to about 15% by weight, wherein the propellant is a hydrofluoroalkane;
a preservative, from about 0.005% to about 3.0% by weight; and
isopropyl myristate, from about 10% to about 35% by weight.

A composition consisting of water, from about 15% to about 40% by weight;
a co-surfactant, from about 10% to about 20% by weight;

an active agent, from about 0.01% to about 10% by weight;
a surfactant, from about 15% to about 40% by weight;
a propellant, from about 5% to about 15% by weight, wherein the propellant is a hydrofluoroalkane;
a preservative, from about 0.005% to about 3.0% by weight; and
isopropyl myristate, from about 10% to about 35% by weight.

In certain embodiments, the present invention relates to any one of the above-mentioned compositions, wherein the composition does not comprise ethanol.

In certain embodiments, the present invention relates to any one of the above-mentioned compositions, wherein water is present in a quantity from about 17% to about 25% by weight. In certain embodiments, the present invention relates to any one of the above-mentioned compositions, wherein water is present in a quantity from about 18% to about 24% by weight. In certain embodiments, the present invention relates to any one of the above-mentioned compositions, wherein water is present in about 18%, about 19%, about 20%, about 21%, about 22%, about 23%, or about 24% by weight. In certain embodiments, the present invention relates to any one of the above-mentioned compositions, wherein water is present in about 18% by weight. In certain embodiments, the present invention relates to any one of the above-mentioned compositions, wherein water is present in about 20% by weight. In certain embodiments, the present invention relates to any one of the above-mentioned compositions, wherein water is present in about 24% by weight.

In certain embodiments, the present invention relates to any one of the above-mentioned compositions, wherein the co-surfactant is ethylene glycol, propylene glycol, or glycerol.

In certain embodiments, the present invention relates to any one of the above-mentioned compositions, wherein the co-surfactant is propylene glycol.

In certain embodiments, the present invention relates to any one of the above-mentioned compositions, wherein the co-surfactant is present in a quantity from about 11% to about 18% by weight. In certain embodiments, the present invention relates to any one of the above-mentioned compositions, wherein the co-surfactant is present in a quantity from about 12% to about 17% by weight. In certain embodiments, the present invention relates to any one of the above-mentioned compositions, wherein the co-surfactant is present in about 13%, about 14%, about 15%, or about 16% by weight. In certain embodiments, the present invention relates to any one of the above-mentioned compositions, wherein the co-surfactant is present in about 13% by weight. In certain embodiments, the present invention relates to any one of the above-mentioned compositions, wherein the co-surfactant is present in about 14% by weight. In certain embodiments, the present invention relates to any one of the above-mentioned compositions, wherein the co-surfactant is present in about 15% by weight. In certain embodiments, the present invention relates to any one of the above-mentioned compositions, wherein the co-surfactant is present in about 16% by weight.

In certain embodiments, the present invention relates to any one of the above-mentioned compositions, wherein the active agent is selected from the group consisting of an antibiotic agent, an anti-inflammatory agent, an anesthetic, an antimicrobial agent, and a keratolytic agent.

In certain embodiments, the present invention relates to any one of the above-mentioned compositions, wherein the active agent is present in a quantity from about 0.05% to about 8.0% by weight. In certain embodiments, the present invention relates to any one of the above-mentioned compositions, wherein the active agent is present in a quantity from about 0.06% to about 7% by weight. In certain embodiments, the present invention relates to any one of the above-mentioned compositions, wherein the active agent is present in about 0.06%, about 0.07%, about 0.08%, about 0.1%, about 0.2%, about 0.3%, about 0.4%, about 0.5%, about 0.6%, about 0.7%, about 0.8%, about 0.9%, about 1.0%, about 1.5%, about 2.0%, about 2.5%, about 3.0%, about 3.5%, about 4.0%, about 4.5%, about 5.0%, about 5.5%, about 6.0%, about 6.5%, or about 7.0% by weight.

In certain embodiments, the present invention relates to any one of the above-mentioned compositions, wherein the active agent is an anesthetic.

In certain embodiments, the present invention relates to any one of the above-mentioned compositions, wherein the anesthetic is lidocaine.

In certain embodiments, the present invention relates to any one of the above-mentioned compositions, wherein the anesthetic is present in a quantity from about 1% to about 6% by weight. In certain embodiments, the present invention relates to any one of the above-mentioned compositions, wherein the anesthetic is present in a quantity from about 2% to about 5% by weight. In certain embodiments, the present invention relates to any one of the above-mentioned compositions, wherein the anesthetic is present in about 2.0%, about 2.5%, about 3.0%, about 3.5%, about 4.0%, about 4.5%, or about 5.0% by weight. In certain embodiments, the present invention relates to any one of the above-mentioned compositions, wherein the anesthetic is present in about 3.5% by weight. In certain embodiments, the present invention relates to any one of the above-mentioned compositions, wherein the anesthetic is present in about 4.0% by weight. In certain embodiments, the present invention relates to any one of the above-mentioned compositions, wherein the anesthetic is present in about 4.5% by weight.

In certain embodiments, the present invention relates to any one of the above-mentioned compositions, wherein the active agent is an anti-inflammatory agent.

In certain embodiments, the present invention relates to any one of the above-mentioned compositions, wherein the anti-inflammatory agent is a non-steroidal anti-inflammatory agent or a steroidal anti-inflammatory agent.

In certain embodiments, the present invention relates to any one of the above-mentioned compositions, wherein the steroidal anti-inflammatory agent is triamcinolone acetonide or betamethasone dipropionate.

In certain embodiments, the present invention relates to any one of the above-mentioned compositions, wherein the steroidal anti-inflammatory agent is triamcinolone acetonide.

In certain embodiments, the present invention relates to any one of the above-mentioned compositions, wherein the steroidal anti-inflammatory agent is betamethasone dipropionate.

In certain embodiments, the present invention relates to any one of the above-mentioned compositions, wherein the anti-inflammatory agent is present in a quantity from about 0.05% to about 1.5% by weight. In certain embodiments, the present invention relates to any one of the above-mentioned compositions, wherein the anti-inflammatory agent is present in a quantity from about 0.06% to about 1.0% by weight. In certain embodiments, the present invention relates to any one of the above-mentioned compositions, wherein the anti-inflammatory agent is present in about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1.0% by weight. In certain embodiments, the present invention relates to any one of the above-mentioned compositions, wherein the anti-inflammatory agent is present in about 0.08% by weight. In certain embodiments, the present invention relates to any one of the above-mentioned compositions, wherein the anti-inflammatory agent is present in about 0.09% by weight. In certain embodiments, the present invention relates to any one of the above-mentioned compositions, wherein the anti-inflammatory agent is present in about 0.1% by weight.

In certain embodiments, the present invention relates to any one of the above-mentioned compositions, wherein the active agent is a keratolytic agent.

In certain embodiments, the present invention relates to any one of the above-mentioned compositions, wherein the keratolytic agent is salicylic acid.

In certain embodiments, the present invention relates to any one of the above-mentioned compositions, wherein the keratolytic agent is present in a quantity from about 2.0% to about 8.0% by weight. In certain embodiments, the present invention relates to any one of the above-mentioned compositions, wherein the keratolytic agent is present in a quantity from about 3.0% to about 7.0% by weight. In certain embodiments, the present invention relates to any one of the above-mentioned compositions, wherein the keratolytic agent is present in about 3.0%, about 3.5%, about 4.0%, about 4.5%, about 5.0%, about 5.5%, about 6.0%, about 6.5%, or about 7.0% by weight. In certain embodiments, the present invention relates to any one of the above-mentioned compositions, wherein the keratolytic agent is present in about 5.0% by weight. In certain embodiments, the present invention relates to any one of the above-mentioned compositions, wherein the keratolytic agent is present in about 5.5% by weight. In certain embodiments, the present invention relates to any one of the above-mentioned compositions, wherein the keratolytic agent is present in about 6.0% by weight.

In certain embodiments, the present invention relates to any one of the above-mentioned compositions, wherein the active agent is a skin-soothing agent.

In certain embodiments, the present invention relates to any one of the above-mentioned compositions, wherein the skin-soothing agent is aloe vera.

In certain embodiments, the present invention relates to any one of the above-mentioned compositions, wherein the skin-soothing agent is present in a quantity from about 0.05% to about 2.0% by weight. In certain embodiments, the present invention relates to any one of the above-mentioned compositions, wherein the skin-soothing agent is present in a quantity from about 0.08% to about 1.5% by weight. In certain embodiments, the present invention relates to any one of the above-mentioned compositions, wherein the skin-soothing agent is present in about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, or about 1.5% by weight. In certain embodiments, the present invention relates to any one of the above-mentioned compositions, wherein the skin-soothing agent is present in about 0.08% by weight. In certain embodiments, the present invention relates to any one of the above-mentioned compositions, wherein the skin-soothing agent is present in about 0.09% by weight. In certain embodiments, the present invention relates to any one of the above-mentioned compositions, wherein the skin-soothing agent is present in about 0.1% by weight.

In certain embodiments, the present invention relates to any one of the above-mentioned compositions, further comprising a second active agent.

In certain embodiments, the present invention relates to any one of the above-mentioned compositions, wherein the surfactant is selected from the group consisting of polysorbates, sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, and methylbenzethonium chloride In certain embodiments, the present invention relates to any one of the above-mentioned compositions, wherein the surfactant is a polysorbate.

In certain embodiments, the present invention relates to any one of the above-mentioned compositions, wherein the surfactant is polysorbate 80.

In certain embodiments, the present invention relates to any one of the above-mentioned compositions, wherein the surfactant is present in a quantity from about 32% to about 39% by weight. In certain embodiments, the present invention relates to any one of the above-mentioned compositions, wherein the surfactant is present in a quantity from about 33% to about 39% by weight. In certain embodiments, the present invention relates to any one of the above-mentioned compositions, wherein the surfactant is present in about 33%, about 34%, about 35%, about 36%, about 37%, about 38%, or about 39% by weight. In certain embodiments, the present invention relates to any one of the above-mentioned compositions, wherein the surfactant is present in about 34% by weight. In certain embodiments, the present invention relates to any one of the above-mentioned compositions, wherein the surfactant is present in about 36% by weight. In certain embodiments, the present invention relates to any one of the above-mentioned compositions, wherein the surfactant is present in about 38% by weight.

In certain embodiments, the present invention relates to any one of the above-mentioned compositions, wherein the hydrofluoroalkane is 1,1,1,2,3,3,3-heptafluoropropane, 1,1,1,2-tetrafluoroethane, or a mixture thereof.

In certain embodiments, the present invention relates to any one of the above-mentioned compositions, wherein the hydrofluoroalkane is 1,1,1,2-tetrafluoroethane.

In certain embodiments, the present invention relates to any one of the above-mentioned compositions, wherein the propellant is present in a quantity from about 5% to about 13% by weight. In certain embodiments, the present invention relates to any one of the above-mentioned compositions, wherein the propellant is present in a quantity from about 6% to about 13% by weight. In certain embodiments, the present invention relates to any one of the above-mentioned compositions, wherein the propellant is present in about 6%, about 7%, about 8%, about 9%, about 10%, about 11%, about 12%, or about 13% by weight. In certain embodiments, the present invention relates to any one of the above-mentioned compositions, wherein the propellant is present in about 6% by weight. In certain embodiments, the present invention relates to any one of the above-mentioned compositions, wherein the propellant is present in about 12% by weight.

In certain embodiments, the present invention relates to any one of the above-mentioned compositions, wherein the preservative is selected from the group consisting of ureas; phenoxyethanol; sodium methyl paraben, methylparaben, ethylparaben, and propylparaben; potassium sorbate; sodium benzoate; citric acid; chlorine dioxide; quaternary ammonium compounds; mercurial agents; and alcoholic agents.

In certain embodiments, the present invention relates to any one of the above-mentioned compositions, wherein the preservative is a quaternary ammonium compound, an alcoholic agent, or a combination of both.

In certain embodiments, the present invention relates to any one of the above-mentioned compositions, wherein the preservative is benzalkonium chloride.

In certain embodiments, the present invention relates to any one of the above-mentioned compositions, wherein the preservative is benzyl alcohol.

In certain embodiments, the present invention relates to any one of the above-mentioned compositions, wherein the preservative is a combination of benzalkonium chloride and benzyl alcohol.

In certain embodiments, the present invention relates to any one of the above-mentioned compositions, wherein the preservative is present in a quantity from about 0.005% to about 3% by weight. In certain embodiments, the present invention relates to any one of the above-mentioned compositions, wherein the preservative is present in a quantity from about 0.01% to about 2.5% by weight. In certain embodiments, the present invention relates to any one of the above-mentioned compositions, wherein the preservative is present in about 0.01%, about 0.02%, about 0.03%, about 0.04%, about 0.05%, about 0.06%, about 0.07%, about 0.08%, about 1.0%, about 1.5%, about 2.0%, or about 2.5% by weight.

In certain embodiments, the present invention relates to any one of the above-mentioned compositions, wherein the benzalkonium chloride is present in a quantity from about 0.008% to about 0.08% by weight. In certain embodiments, the present invention relates to any one of the above-mentioned compositions, wherein the benzalkonium chloride is present in about 0.008%, about 0.009%, about 0.01%, about 0.02%, about 0.03%, about 0.04%, about 0.05%, about 0.06%, about 0.07%, or about 0.08% by weight. In certain embodiments, the present invention relates to any one of the above-mentioned compositions, wherein the benzalkonium chloride is present in about 0.01% by weight. In certain embodiments, the present invention relates to any one of the above-mentioned compositions, wherein the benzalkonium chloride is present in about 0.02% by weight. In certain embodiments, the present invention relates to any one of the above-mentioned compositions, wherein the benzalkonium chloride is present in about 0.04% by weight.

In certain embodiments, the present invention relates to any one of the above-mentioned compositions, wherein the benzyl alcohol is present in a quantity from about 0.8% to about 3.0% by weight. In certain embodiments, the present invention relates to any one of the above-mentioned compositions, wherein the benzyl alcohol is present in a quantity from about 1.2% to about 2.5% by weight. In certain embodiments, the present invention relates to any one of the above-mentioned compositions, wherein the benzyl alcohol is present in about 1.2%, about 1.3%, about 1.4%, about 1.5%, about 1.6%, about 1.7%, about 1.8%, about 1.9%, about 2.0%, about 2.1%, about 2.2%, about 2.3%, about 2.4% or about 2.5% by weight. In certain embodiments, the present invention relates to any one of the above-mentioned compositions, wherein the benzyl alcohol is present in about 1.4% by weight. In certain embodiments, the present invention relates to any one of the above-mentioned compositions, wherein the benzyl alcohol is present in about 1.5% by weight. In certain embodiments, the present invention relates to any one of the above-mentioned compositions, wherein the benzyl alcohol is present in about 2.1% by weight.

In certain embodiments, the invention relates to a composition comprising
    water, in about 20% by weight;
    a co-surfactant, in about 14% by weight, wherein the co-surfactant is propylene glycol;
    an active agent, in about 4.0% by weight, wherein the active agent is lidocaine;
    a surfactant, in about 39% by weight, wherein the surfactant is polysorbate 80;
    a propellant, in about 6% by weight, wherein the propellant is 1,1,1,2-tetrafluoroethane;
    a preservative, wherein the preservative is benzalkonium chloride, in about 0.04% by weight, and benzyl alcohol, in about 1.9% by weight; and
    isopropyl myristate, in about 15% by weight.

In certain embodiments, the invention relates to a composition consisting essentially of water, in about 20% by weight;
    a co-surfactant, in about 14% by weight, wherein the co-surfactant is propylene glycol;
    an active agent, in about 4.0% by weight, wherein the active agent is lidocaine;
    a surfactant, in about 39% by weight, wherein the surfactant is polysorbate 80;
    a propellant, in about 6% by weight, wherein the propellant is 1,1,1,2-tetrafluoroethane;
    a preservative, wherein the preservative is benzalkonium chloride, in about 0.04% by weight, and benzyl alcohol, in about 1.9% by weight; and
    isopropyl myristate, in about 15% by weight.

In certain embodiments, the invention relates to a composition consisting of water, in about 20% by weight;
    a co-surfactant, in about 14% by weight, wherein the co-surfactant is propylene glycol;
    an active agent, in about 4.0% by weight, wherein the active agent is lidocaine;
    a surfactant, in about 39% by weight, wherein the surfactant is polysorbate 80;
    a propellant, in about 6% by weight, wherein the propellant is 1,1,1,2-tetrafluoroethane;
    a preservative, wherein the preservative is benzalkonium chloride, in about 0.04% by weight, and benzyl alcohol, in about 1.9% by weight; and
    isopropyl myristate, in about 15% by weight.

In certain embodiments, the present invention relates to a composition comprising
    water, in about 19% by weight;
    a co-surfactant, in about 13% by weight, wherein the co-surfactant is propylene glycol;
    an active agent, in about 5% by weight, wherein the active agent is salicylic acid;
    a surfactant, in about 36% by weight, wherein the surfactant is polysorbate 80;
    a propellant, in about 12% by weight, wherein the propellant is 1,1,1,2-tetrafluoroethane;
    isopropyl myristate, in about 14% by weight; and
    a second active agent, in about 0.09% by weight, wherein the second active agent is aloe vera.

In certain embodiments, the present invention relates to a composition consisting essentially of
    water, in about 19% by weight;
    a co-surfactant, in about 13% by weight, wherein the co-surfactant is propylene glycol;
    an active agent, in about 5% by weight, wherein the active agent is salicylic acid;
    a surfactant, in about 36% by weight, wherein the surfactant is polysorbate 80;

a propellant, in about 12% by weight, wherein the propellant is 1,1,1,2-tetrafluoroethane;
isopropyl myristate, in about 14% by weight; and
a second active agent, in about 0.09% by weight, wherein the second active agent is aloe vera.

In certain embodiments, the present invention relates to a composition consisting of
water, in about 19% by weight;
a co-surfactant, in about 13% by weight, wherein the co-surfactant is propylene glycol;
an active agent, in about 5% by weight, wherein the active agent is salicylic acid;
a surfactant, in about 36% by weight, wherein the surfactant is polysorbate 80;
a propellant, in about 12% by weight, wherein the propellant is 1,1,1,2-tetrafluoroethane;
isopropyl myristate, in about 14% by weight; and
a second active agent, in about 0.09% by weight, wherein the second active agent is aloe vera.

In certain embodiments, the present invention relates to a composition comprising water, in about 20% by weight;
a co-surfactant, in about 14% by weight, wherein the co-surfactant is propylene glycol;
an active agent, in about 0.09% by weight, wherein the active agent is triamcinolone acetonide;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to a composition consisting essentially of water, in about 20% by weight;
a co-surfactant, in about 14% by weight, wherein the co-surfactant is propylene glycol;
an active agent, in about 0.09% by weight, wherein the active agent is triamcinolone acetonide;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to a composition consisting of
water, in about 20% by weight;
a co-surfactant, in about 14% by weight, wherein the co-surfactant is propylene glycol;
an active agent, in about 0.09% by weight, wherein the active agent is triamcinolone acetonide;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to a composition comprising water, in about 20% by weight;
a co-surfactant, in about 14% by weight, wherein the co-surfactant is propylene glycol;
an active agent, in about 0.09% by weight, wherein the active agent is betamethasone dipropionate;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to a composition consisting essentially of
water, in about 20% by weight;
a co-surfactant, in about 14% by weight, wherein the co-surfactant is propylene glycol;
an active agent, in about 0.09% by weight, wherein the active agent is betamethasone dipropionate;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to a composition consisting of
water, in about 20% by weight;
a co-surfactant, in about 14% by weight, wherein the co-surfactant is propylene glycol;
an active agent, in about 0.09% by weight, wherein the active agent is betamethasone dipropionate;
a surfactant, in about 38% by weight, wherein the surfactant is polysorbate 80;
a propellant, in about 12% by weight, wherein the propellant is 1,1,1,2-tetrafluoroethane; and
isopropyl myristate, in about 15% by weight.

In certain embodiments, the present invention relates to any one of the above-mentioned compositions, wherein the composition is in an aerosol container.

In certain embodiments, the present invention relates to any one of the above-mentioned compositions in the form of a foam. In certain embodiments, the foam is produced by actuation of an aerosol container comprising the composition.

Exemplary Methods of Formulation

In certain embodiments, the present invention relates to a method of making a composition, comprising the steps of
mixing water and a co-surfactant, thereby forming a first solution;
optionally heating the first solution;
adding an active agent to the first solution and mixing, thereby forming a second solution;
adding a component of an oil phase to the second solution and mixing, thereby forming a two-phase mixture;
adding a surfactant to the two-phase mixture and mixing; thereby forming a microemulsion;
adding the microemulsion to an aerosol container; and
pressurizing the aerosol container with a propellant, wherein the propellant is a hydrofluoroalkane.

In certain embodiments, the present invention relates to any one of the above-mentioned methods, wherein the component of the oil phase is selected from the group consisting of mineral oil, emollient oils, saturated fatty acids, unsaturated fatty acids, medium chain-length triglycerides, isopropyl myristate, isopropyl palmitate, oleic acid, isostearylic isostearate, triacetin, ethyl oleate, and octyl octanoate. In certain embodiments, the present invention relates to any one of the above-mentioned methods, wherein the component of the oil phase is isopropyl myristate.

In certain embodiments, the present invention relates to a method of making a composition, comprising the steps of
mixing water and a co-surfactant, thereby forming a first solution;
optionally heating the first solution;
adding an active agent to the first solution and mixing, thereby forming a second solution;
adding isopropyl myristate to the second solution and mixing, thereby forming a two-phase mixture;

adding a surfactant to the two-phase mixture and mixing; thereby forming a micro emulsion;

adding the microemulsion to an aerosol container; and pressurizing the aerosol container with a propellant, wherein the propellant is a hydrofluoroalkane.

In certain embodiments, the present invention relates to a method of making a composition, comprising the steps of mixing water and a co-surfactant, thereby forming a first solution;

adding a component of an oil phase to the first solution and mixing, thereby forming a two-phase mixture;

adding a surfactant to the two-phase mixture and mixing; thereby forming a microemulsion base;

optionally heating the microemulsion base;

adding an active agent to the microemulsion base and mixing, thereby forming an active agent-containing microemulsion;

adding the active agent-containing microemulsion to an aerosol container; and pressurizing the aerosol container with a propellant, wherein the propellant is a hydrofluoroalkane.

In certain embodiments, the present invention relates to any one of the above-mentioned methods, wherein the component of the oil phase is selected from the group consisting of mineral oil, emollient oils, saturated fatty acids, unsaturated fatty acids, medium chain-length triglycerides, isopropyl myristate, isopropyl palmitate, oleic acid, isostearylic isostearate, triacetin, ethyl oleate, and octyl octanoate. In certain embodiments, the present invention relates to any one of the above-mentioned methods, wherein the component of the oil phase is isopropyl myristate.

In certain embodiments, the present invention relates to a method of making a composition, comprising the steps of mixing water and a co-surfactant, thereby forming a first solution;

adding isopropyl myristate to the first solution and mixing, thereby forming a two-phase mixture;

adding a surfactant to the two-phase mixture and mixing; thereby forming a microemulsion base;

optionally heating the microemulsion base;

adding an active agent to the microemulsion base and mixing, thereby forming an active agent-containing microemulsion;

adding the active agent-containing microemulsion to an aerosol container; and pressurizing the aerosol container with a propellant, wherein the propellant is a hydrofluoroalkane.

Exemplary Methods of Use

In certain embodiments, the present invention relates to a method of treating the skin of a subject, comprising the step of applying to the skin of a subject in need thereof any one of the above-mentioned compositions.

In certain embodiments, the present invention relates to any one of the above-mentioned methods, wherein the subject is suffering from a dermatological condition. In certain embodiments, the present invention relates to any one of the above-mentioned methods, wherein the subject is suffering from a dermatological condition selected from the group consisting of a bacterial infection, a viral infection, a fungal infection, inflammation, dandruff, cradle cap, warts, seborrheic dermatitis, pain, and acne. In certain embodiments, the present invention relates to any one of the above-mentioned methods, wherein the skin of the subject is to be anesthetized. In certain embodiments, the present invention relates to any one of the above-mentioned methods, wherein the skin of the subject is to be softened. In certain embodiments, the present invention relates to any one of the above-mentioned methods, wherein the skin of the subject is to be shed.

EXEMPLIFICATION

The invention now being generally described, it will be more readily understood by reference to the following examples which are included merely for purposes of illustration of certain aspects and embodiments of the present invention, and are not intended to limit the invention.

In the Examples given below, model compounds were used as active agents. It is understood, however, that any one or more of numerous compounds can be incorporated into foamable stable microemulsion compositions for topical administration using methods and techniques described herein.

Example 1

Lidocaine-containing Foamable Microemulsion Composition with Ethyl Alcohol

An oil-in-water microemulsion was formed spontaneously when aqueous/co-surfactant, oil, and surfactant phases were mixed together in appropriate concentrations. The formed microemulsion was clear, optically isotropic and thermodynamically stable. The microemulsion was placed in an aerosol container and charged with 1,1,1,2-tetrafluoroethane (HFA 134a) propellant resulting in thermodynamically-stable, clear composition that dispensed as foam upon actuation.

The following manufacturing procedure was followed for preparation of various microemulsion concentrates and foamable microemulsion compositions: required quantities of DI water and ethyl alcohol (or glycol when ethanol-free compositions were made) were mixed in a container. Isopropyl Myristate was slowly added to the aqueous phase forming two-phase system. Then, polysorbate 80 was slowly added to two-phase system while mixing with prop mixer. Mixing was continued until a clear solution was formed. To this microemulsion, 4% lidocaine was added and mixed with prop mixer until all drug was completely dissolved. Finally, 0.04% benzalkonium chloride was added as a preservative. The obtained drug-containing microemulsion concentrate was filled into a glass aerosol container and charged with HFA 134a in the range 6 to 12% (w/w). The single phase was formed and no phase separation was observed during the stability study at both, room temperature and 40° C.

Foamable Microemulsion Composition #1

| Ingredient | %, w/w |
|---|---|
| DI water | 24.06 |
| Isopropyl Myristate | 14.10 |
| Polysorbate 80 | 34.50 |
| Ethyl alcohol | 15.90 |
| Benzyl alcohol | 1.40 |
| Benzalkonium chloride | 0.04 |
| HFA 134a | 6.00 |
| Lidocaine | 4.00 |
| Total | 100.00 |

Foamable Active Agent-containing Microemulsion Concentrate

| Ingredient | %, w/w |
|---|---|
| DI water | 25.66 |
| Isopropyl Myristate | 15.04 |
| Polysorbate 80 | 36.80 |
| Ethyl alcohol | 16.96 |
| Benzyl alcohol | 1.5 |
| Benzalkonium chloride | 0.04 |
| Lidocaine | 4.00 |
| Total | 100.00 |

Example 2

Lidocaine-containing Foamable Microemulsion Composition without Ethyl Alcohol

Due to potential flammability hazard issues with ethyl alcohol at large scales and undesirable ethanol skin-drying properties, oil-in-water microemulsion was formulated without ethyl alcohol. Propylene glycol, glycerin and ethylene glycol were examined as ethyl alcohol replacements. Despite the fact that Hsiu-O et al. suggest that short chain alcohols (i.e., ethyl alcohol) are required as co-surfactants for producing microemulsions, we were able to formulate stable microemulsion concentrates and foamable microemulsion compositions without ethyl alcohol. Microemulsion concentrate #2 was charged with HFA 134a, and a single-phase system was formed that upon actuation produced foam. HFA 134a level was 6% (w/w).

Microemulsion Concentrate #2

| Ingredient | %, w/w |
|---|---|
| Propylene Glycol | 15.00 |
| DI Water | 21.50 |
| Lidocaine | 4.00 |
| Polysorbate 80 | 41.10 |
| Isopropyl Myristate | 16.30 |
| Benzalkonium Chloride | 0.02 |
| Benzyl Alcohol | 2.06 |
| Total | 100.00 |

Example 3

Microemulsions with Water, Isopropyl Myristate, and Polysorbate 80/Ethanol Mixture Using ethanol as a co-surfactant, a ternary phase diagram was identified showing the combinations of water, oil and surfactant/co-surfactant under which a clear microemulsion system can be formulated. FIG. 1 shows the phase diagram of microemulsion systems indicating the emulsion/microemulsion phase boundary at various concentrations of water, isopropyl myristate (IPM), and polysorbate 80:ethanol (2:1). Polysorbate 80 is also referred to as "Tween® 80" or "Tween 80" and vice versa. The concentrations of each constituent of the microemulsions are depicted in the following table.

| % Polysorbate 80:Ethanol (2:1) (w/w) | % IPM (w/w) | % DI water (w/w) |
|---|---|---|
| 9.78 | 85.21 | 5.01 |
| 18.65 | 74.42 | 6.93 |
| 27.52 | 64.22 | 8.26 |
| 33.47 | 50.13 | 16.40 |
| 37.75 | 37.71 | 24.54 |
| 40.10 | 26.71 | 33.19 |
| 46.42 | 19.89 | 33.69 |
| 46.68 | 11.77 | 41.55 |
| 46.85 | 5.30 | 47.84 |

Example 4

Figure 2:
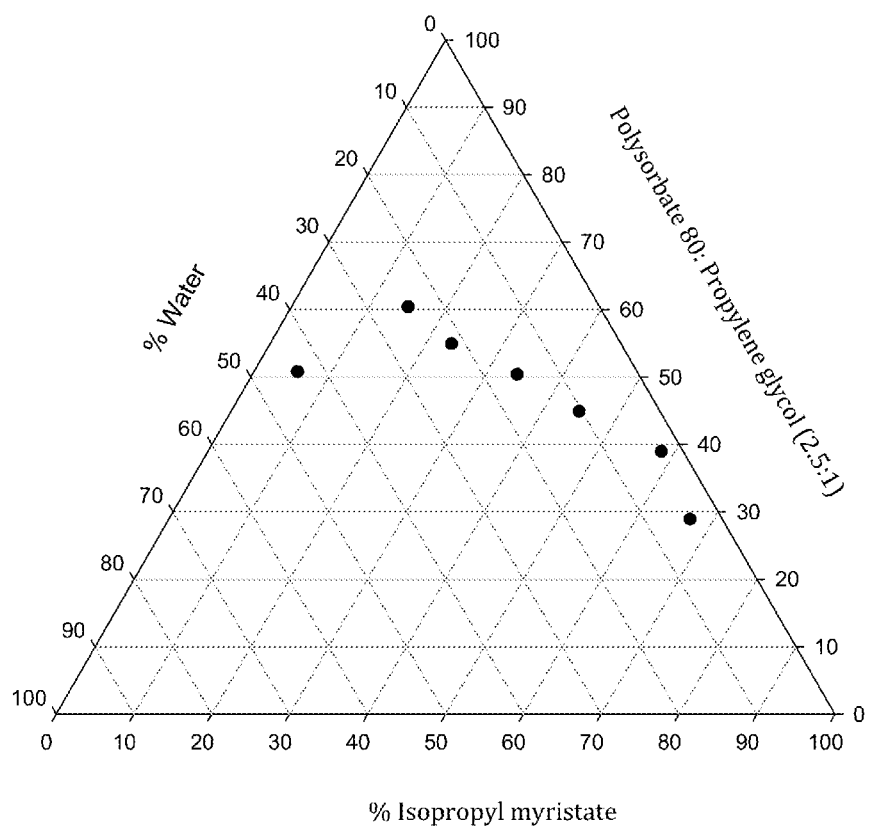
FIG. 2 depicts a ternary phase diagram for microemulsion systems comprising water (left axis), isopropyl myristate (bottom axis), and polysorbate 80:propylene glycol (2.5:1) (right axis).

Microemulsions with Water, Isopropyl Myristate, and Polysorbate 80/Propylene Glycol Mixture FIG. 2 shows the phase diagram of microemulsion systems indicating the emulsion/microemulsion phase boundary at various concentrations of water, isopropyl myristate (IPM), and polysorbate 80:propylene glycol (2.5:1). The concentrations of each constituent of the microemulsions are depicted in the following table.

| % Polysorbate 80:Propylene glycol (2.5:1) (w/w) | % IPM (w/w) | % DI water (w/w) |
|---|---|---|
| 19.18 | 76.57 | 4.26 |
| 28.78 | 67.11 | 4.11 |
| 38.85 | 58.38 | 2.77 |
| 44.77 | 44.86 | 10.37 |
| 50.27 | 34.16 | 15.57 |
| 54.81 | 23.47 | 21.72 |
| 60.30 | 15.14 | 24.56 |
| 50.66 | 5.76 | 43.58 |

Example 5

Salicylic Acid- and Aloe Vera-containing Foamable Microemulsion Composition without Ethyl Alcohol A foamable microemulsion comprising salicylic acid, a keratolytic agent, and aloe vera, a skin-soothing agent, was prepared as follows:

| | Batch size 500 g | |
|---|---|---|
| Ingredient | % w/w | Wt. required (g) |
| Propylene glycol | 15 | 75 |
| DI water | 21.5 | 107.5 |
| Polysorbate 80 | 41.1 | 205.5 |
| Isopropyl Myristate | 16.3 | 81.5 |
| Salicylic acid | 6 | 30 |
| Aloe Vera | 0.1 | 0.5 |
| Total | 100 | 500 |

DI water and propylene glycol were placed into a glass beaker. Mixing was started. The mixture was heated to 65-70° C. Salicylic acid was added and mixing was continued. Once a clear solution was observed, aloe vera was added. Upon dissolution of aloe vera, isopropyl myristate was added, with mixing. A two-phase system was observed. Finally, polysorbate 80 was added to the two-phase system, while mixing. A clear microemulsion was obtained.

Figure 3:
FIG. 3 depicts a salicylic acid and aloe vera microemulsion in a glass aerosol container.
Figure 4:
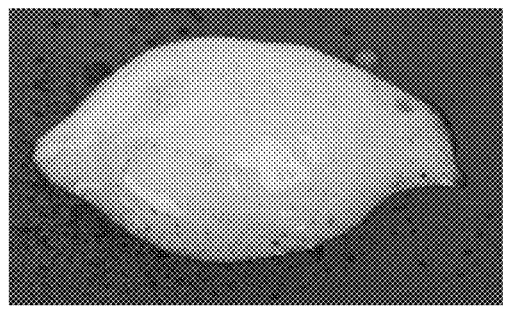
FIG. 4 depicts a foam generated upon actuation of an aerosol container comprising a salicylic acid and aloe vera microemulsion.

The clear microemulsion (50 g) was filled into a glass aerosol container. The container was crimped and pressurized with 7 g of HFA 134a. A clear, homogenous formulation was obtained (FIG. 3). Upon actuation of the aerosol container, foam was produced (FIG. 4).

Example 6

Triamcinolone-containing Foamable Microemulsion Composition without Ethyl Alcohol A foamable microemulsion comprising triamcinolone, a steroidal anti-inflammatory agent, was prepared as follows:

| Batch size 500 g | | |
|---|---|---|
| Ingredient | % w/w | Wt. required (g) |
| Propylene glycol | 15.97 | 79.85 |
| DI water | 22.87 | 114.35 |
| Polysorbate 80 | 43.72 | 218.6 |
| Isopropyl Myristate | 17.34 | 86.7 |
| Triamcinolone acetonide | 0.1 | 0.5 |
| | 100 | 500 |

DI water and propylene glycol were placed into a glass beaker. Mixing was started. The mixture was heated to 65-70° C. Triamcinolone acetonide was added and mixing was continued. Once a clear solution was observed, isopropyl myristate was added, with mixing. A two-phase system was observed. Finally, polysorbate 80 was added to the two-phase system, while mixing. A clear microemulsion was obtained. The final weight may be adjusted with DI water, if necessary.

Figure 5:
FIG. 5 depicts a triamcinolone acetonide microemulsion in a glass aerosol container.
Figure 6:
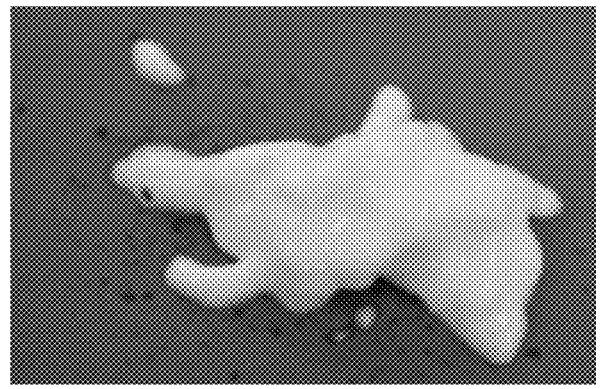
FIG. 6 depicts a foam generated upon actuation of an aerosol container comprising a triamcinolone acetonide microemulsion.

The clear microemulsion (50 g) was filled into a glass aerosol container. The container was crimped and pressurized with 7 g of HFA 134a. A clear, homogenous formulation was obtained (FIG. 5). Upon actuation of the aerosol container, foam was produced (FIG. 6).

Example 7

Betamethasone Dipropionate-containing Foamable Microemulsion Composition without Ethyl Alcohol A foamable microemulsion comprising betamethasone, a steroidal anti-inflammatory agent, was prepared as follows:

| Batch size 500 g | | |
|---|---|---|
| Ingredient | % w/w | Wt. required (g) |
| Propylene glycol | 15.97 | 79.85 |
| DI water | 22.87 | 114.35 |
| Polysorbate 80 | 43.72 | 218.6 |
| Isopropyl Myristate | 17.34 | 86.7 |
| Betamethasone Dipropionate | 0.1 | 0.5 |
| | 100 | 500 |

DI water and propylene glycol were placed into a glass beaker. Mixing was started. Isopropyl myristate was added and mixing was continued. A two-phase system was observed. Polysorbate 80 was added to the two-phase system, while mixing. The resultant mixture was then heated to 50° C. Betamethasone dipropionate was added and mixing was continued. A clear microemulsion was obtained.

Figure 7:
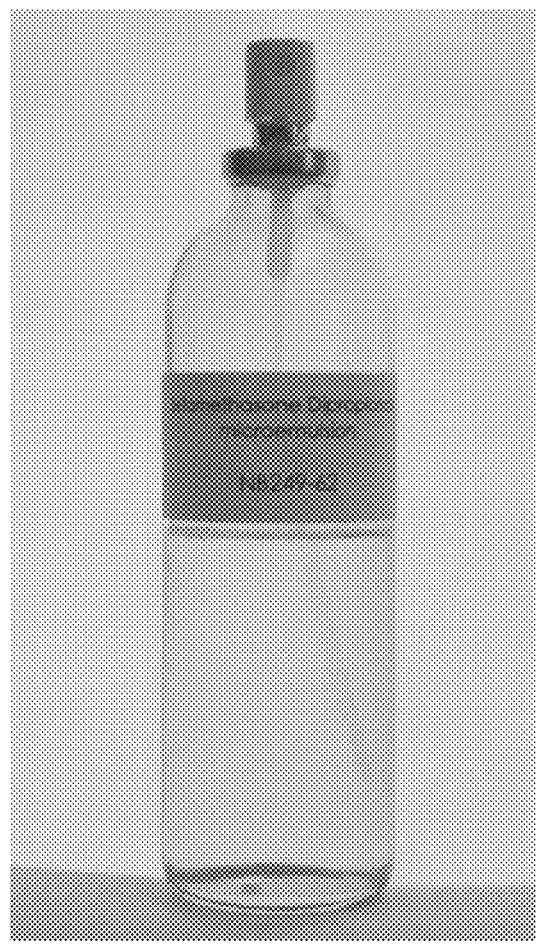
FIG. 7 depicts a betamethasone propionate microemulsion in a glass aerosol container.
Figure 8:
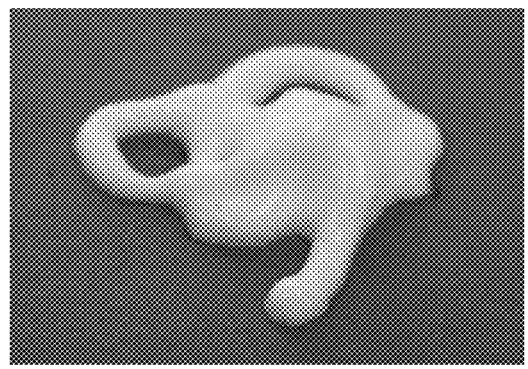
FIG. 8 depicts a foam generated upon actuation an aerosol container comprising a betamethasone propionate microemulsion.

The clear microemulsion (50 g) was filled into a glass aerosol container. The container was crimped and pressurized with 7 g of HFA 134a. A clear, homogenous formulation was obtained (FIG. 7). Upon actuation of the aerosol container, foam was produced (FIG. 8).

REFERENCES CITED

1. Hsiu-O Ho, Chih-Chuan Hsaio, and Ming-Thau Sheu. Preparation of Microemulsions using polyglycerol fatty acid esters as surfactant for delivery of protein drugs. *Journal of Pharmaceutical Sciences*, Vol. 85(2), February 1996, 138-143.
2. Zhinan Mei et al. Solid lipid nanoparticle and microemulsion for topical delivery of triptolide. *European Journal of Pharmaceutics and Biopharmaceutics* 56 (2003) 189-196.
3. Philip J. Lee, Robert Langer, and V. Prasad Shastri. Novel microemulsion enhancer formulation for simultaneous transdermal delivery of hydrophilic and hydrophobic drugs. *Pharmaceutical Research*, Vol 20, February 2003, 264-269.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method of locally anesthetizing the skin of a subject, comprising the step of
  applying topically to the skin of a subject in need thereof an effective amount of a composition comprising
    water, in a quantity from about 15% to about 40% by weight of the composition;
    propylene glycol, in a quantity from about 11% to about 18% by weight of the composition;
    lidocaine, in a quantity from about 1% to about 6% by weight of the composition;
    polysorbate 80, in a quantity from about 32% to about 39% by weight of the composition;
    1,1,1,2-tetrafluoroethane, in a quantity from about 5% to about 13% by weight of the composition;
    benzalkonium chloride, in a quantity from about 0.008% to about 0.08% by weight of the composition;
    benzyl alcohol, in a quantity from about 0.8% to about 3.0% by weight of the composition; and
    isopropyl myristate, in a quantity from about 10% to about 35% by weight of the composition;
  wherein
    the water, the propylene glycol, the lidocaine, the polysorbate 80, the benzalkonium chloride, the benzyl alcohol, and the isopropyl myristate form a microemulsion;
    the microemulsion is optically clear and optically isotropic;
    the composition is a single phase; and
    the composition is optically clear.

2. The method of claim 1, wherein the composition comprises:
- water, in about 20% by weight of the composition;
- propylene glycol, in about 14% by weight of the composition;
- lidocaine, in about 4.0% by weight of the composition;
- polysorbate 80, in about 39% by weight of the composition;
- 1,1,1,2-tetrafluoroethane, in about 6% by weight of the composition;
- benzalkonium chloride, in about 0.04% by weight of the composition;
- benzyl alcohol, in about 1.9% by weight of the composition; and
- isopropyl myristate, in about 15% by weight of the composition.

\* \* \* \* \*